(12) United States Patent
Wagner

(10) Patent No.: US 6,620,390 B1
(45) Date of Patent: Sep. 16, 2003

(54) STERILIZING CONTAINER

(75) Inventor: Peter Wagner, Starnberg (DE)

(73) Assignee: Wagner GmbH Fabrik fur Medizinische Gerate (DE)

( * ) Notice: Subject to any disclaimer, the term of this patent is extended or adjusted under 35 U.S.C. 154(b) by 0 days.

(21) Appl. No.: 09/555,547

(22) PCT Filed: Nov. 30, 1998

(86) PCT No.: PCT/EP98/07746

§ 371 (c)(1),
(2), (4) Date: Jul. 24, 2000

(87) PCT Pub. No.: WO99/27969

PCT Pub. Date: Jun. 10, 1999

(30) Foreign Application Priority Data

Dec. 3, 1997 (DE) .......................... 197 53 671

(51) Int. Cl.[7] ................................ A61L 2/00
(52) U.S. Cl. .................. 422/297; 206/325; 206/435; 422/292; 422/300
(58) Field of Search ................ 422/292, 297, 422/300; 206/325, 435

(56) References Cited

U.S. PATENT DOCUMENTS

| | | | | |
|---|---|---|---|---|
| 4,512,498 A | * | 4/1985 | Leibinger | 220/371 |
| 4,551,311 A | * | 11/1985 | Lorenz | 220/256.1 |
| 4,584,182 A | * | 4/1986 | Sanderson et al. | 220/203.12 |
| 5,019,345 A | 5/1991 | Lorenz | 422/26 |
| 5,202,098 A | * | 4/1993 | Nichols | 206/363 |
| 5,968,459 A | * | 10/1999 | Nalepa et al. | 206/439 |

FOREIGN PATENT DOCUMENTS

| | | |
|---|---|---|
| DE | 1217550 | 5/1966 |
| DE | 1217551 | 5/1966 |
| DE | 1642161 | 8/1970 |
| DE | 3202430 | 7/1983 |
| DE | 3438463 | 4/1986 |
| DE | 4125673 | 7/1992 |
| EP | 0152544 | 8/1985 |

* cited by examiner

*Primary Examiner*—Krisanne Thornton
(74) *Attorney, Agent, or Firm*—Ostrolenk, Faber, Gerb & Soffen, LLP (57) ABSTRACT

A sterilizing container for holding surgical instruments or other sterilizing material during sterilization and for maintaining the sterilized condition during storage and transportation. The container has a body portion with at least one opening to permit exchange of media during the sterilization process. The filter is fitted in a sealing manner into the opening and permits at least a limited exchange of media and forms a barrier to microorganisms during storage. A self-closing inlet valve is provided so as to open toward the inside of the container when a predetermined pressure difference between external pressure and internal pressure is exceeded. A self-closing outlet valve is provided so as to open outward when a predetermined pressure difference between internal pressure and external pressure is exceeded. The filter is clamped in a holding frame and is supported all around on the holding frame with a form fit. The holding frame in turn is clamped on the edge of the container opening. At least the inward valve is arranged inside the holding frame.

20 Claims, 9 Drawing Sheets

STERILIZING CONTAINER

BACKGROUND OF THE INVENTION

The invention relates to a-sterilizing container for holding surgical instruments or other sterilizing material during sterilization and for maintaining the sterilized condition during storage and transportation. During sterilization, such sterilizing containers must permit exchange of media inside the sterilizer.

In order to permit exchange of media, it is known to equip the sterilizing containers with double valves which, during the sterilizing process in the sterilizer, alternately open and close depending on the pressure difference, and which, after the sterilizing process, remain closed in order to protect the sterilized material from penetration of microorganisms during storage. Such sterilizing containers are known, for example, from DE-B 1,217,550, DE-B 1,217,551 and DE Patent 1,642,161 and DE Patent 3,202,430. Other known sterilizing containers have container openings which are equipped with a filter through which the exchange of media takes place during the sterilizing process in the sterilizer, and which, after completion of the sterilizing process, are intended to form a barrier to penetration of microorganisms during storage of the sterilizing container. Such sterilizing containers are known, for example, from DE 3,438,463 C2. From this patent specification, it is also known to mount a filter leaf and a spring-preloaded filter holder plate in such a way that when a predetermined pressure difference is exceeded, the filter leaf can be lifted up like a valve from the cover openings, thus establishing a secondary flow route. A bypass is thus created as soon as the external pressure becomes so high that there is a danger of the container being squeezed together.

Such an overpressure valve is also proposed in DE 4,125,673 C1. This overpressure valve, which opens toward the inside of the container when a predetermined external pressure is established, can be pushed into a guide on the container wall. A filter assigned to a further container opening can be pushed into a similar guide.

This valve/filter combination known from DE 4,125,673 C1 and other valve/filter combinations are intended only as protective means for preventing the container from being squeezed together.

In sterilizing containers equipped with filters, the exchange of media in the sterilizer was intended to take place through these filters. The filters were accordingly designed in such a way that they could compensate sufficiently quickly for the pressure differences which occurred. This entailed a corresponding pore size which, although small enough to protect the container contents from dust and large-volume microorganisms, was unable to guarantee that no microorganisms could get in, particularly extremely small viruses or fungal spores. Thus, in the sterilizing containers equipped with filters, there was, over the course of time, an increasing risk of penetration of microorganisms.

SUMMARY OF THE INVENTION

The invention is therefore based on the object of making available a sterilizing container equipped with filters, in which the filter has fine pores and is designed in such a way that there is no penetration of microorganisms after sterilization, even after long storage periods, but in which the short-term pressure differences occurring in modern autoclaves can be reduced without damage to filter or container.

Thus, according to the invention, in addition to the filter, inlet and outlet valves are provided which are also intended to act during the sterilizing process and do not serve merely as safety valves, and which come into action as soon as the pressure difference from outside to inside or from inside to outside has become so great that the exchange of media through the filter material cannot take place sufficiently quickly.

Accordingly, the invention is based on the knowledge that sterilizing containers can be equipped with filters of any desired fineness if care is taken to ensure that a bypass is created in both directions, i.e. not only from outside to inside, but also from inside to outside, when a pressure difference predetermined by the structure is exceeded.

According to a preferred embodiment of the invention, filter and valves are arranged in a common container opening, for example in an opening of an intermediate cover, provided with a protective cover, or in a container wall or in the bottom. A particularly expedient and robust construction is obtained if the filter is clamped immovably in a holding frame and at least one of the valves is integrated in the holding frame, which in turn is braced firmly on the opening edge. For the invention, however, the possibility should be left open to arrange the filter and at least one of the valves in different container openings, which can be expedient, for example, if a condensate bleeder valve is to be arranged on the bottom of the sterilizing container. This condensate bleeder valve can then be designed at the same time as an overpressure valve, via which an increased internal pressure in the container can be reduced.

The two valves can be integrated in the holding frame of the filter in such a way that there are no outwardly movable parts which could come into contact with the container contents and which could be manipulated from outside.

According to the invention, the filter material can have almost any desired flow resistance, and it cannot slip, thus ruling out the danger of an open bypass remaining after completion of the sterilizing process.

Compared to the known spring-mounted filter holder plates in which the filter is opened during occurrence of the bypass flow and, on account of the flow, can slip into another position or become stuck, the filter in the arrangement according to the invention always provides correct sealing. According to the invention, the whole arrangement (bypass with filter) is immovable, which results in a dual safety advantage:

a) the function of the bypass cannot be blocked by the container contents;

b) the bypass cannot be inadvertently actuated by the container contents or from outside.

According to the invention, all known filter materials can be used, for example surface filters made of paper, synthetics or textile, and also membrane filters or 3D volume filters and submicron particulate filters, by which even viruses or fungal spores can be held back.

Preferred designs of the filter/valve combination are set out in the dependent claims and in the description of illustrative embodiments.

BRIEF DESCRIPTION OF THE DRAWINGS

Illustrative embodiments of the invention are described below with reference to the drawing, in which:

FIG. 6 shows a section along the line VI—VI according to FIG. 7;

FIG. 7 is a plan view of FIG. 6;

FIG. 8 is a view of FIG. 6 from below, FIG. 9 is a section along the line IX—IX according to FIG. 8;

DETAILED DESCRIPTION OF THE PREFERRED EMBODIMENTS

Figure 1:
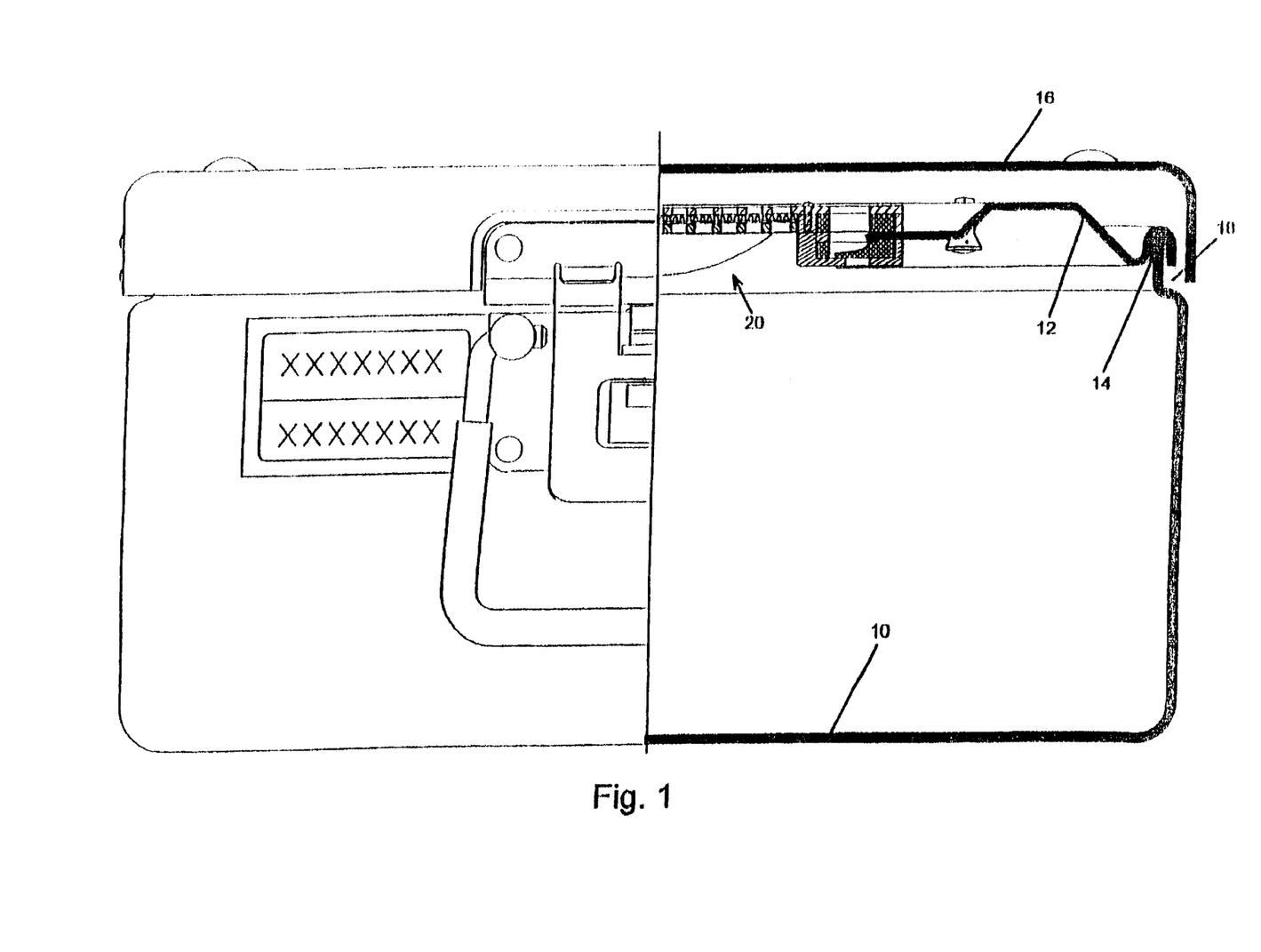
FIG. 1 shows a half cross-sectional view of a sterilizing container according to the invention, with a filter leaf with double valve arrangement incorporated in an intermediate cover.

In terms of its basic.design, the sterilizing container shown in FIG. 1 corresponds to the sterilizing container according to DE 3,146,349 A1, and it consists of a lower part 10 of the container, an intermediate cover 12, which is fitted via a sealing ring 14 onto the inwardly directed edge of the lower part of the container, and a closed container cover 16 which engages over the lower part of the container with intermediate cover and leaves a labyrinth gap 18 free for exchange of media during the sterilizing process in the sterilizer. For the purposes of exchange of media, the intermediate cover has a filter/valve combination 20, which can be seen in detail in FIGS. 2 to 5. This filter/valve combination 20 in the double cover proves expedient because it is protected by the container cover 16 engaging over it. For the invention, however, the possibility should be left open for accommodating such a filter/valve combination at other points of a sterilizing container, for example in the side walls or, in the bottom or in a cover closing the container.

Figure 2:
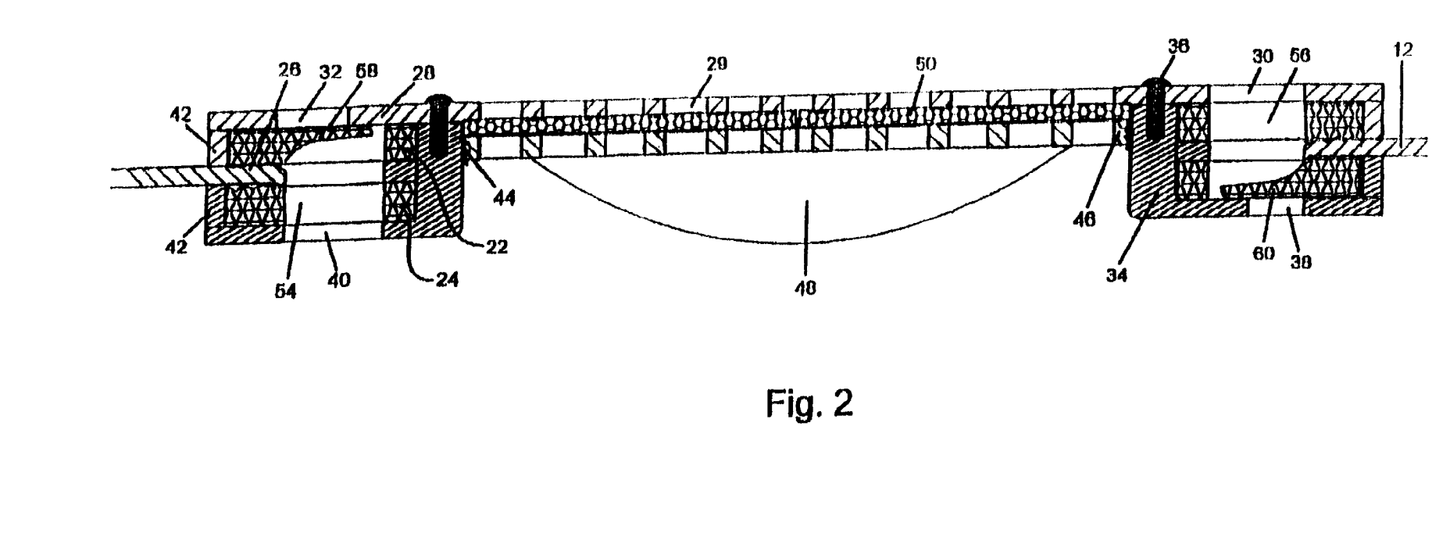
FIG. 2 is a sectional view of the intermediate cover according to FIG. 1.
Figure 3:
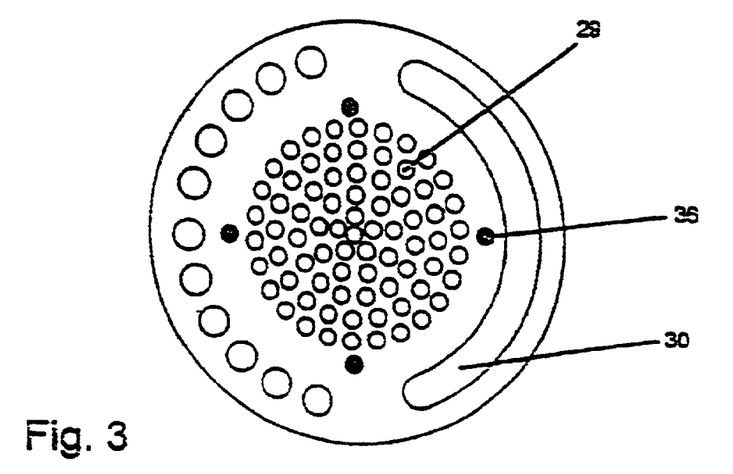
FIG. 3 is a view of the filter/valve arrangement according to FIG. 2, seen from above.
Figure 4:
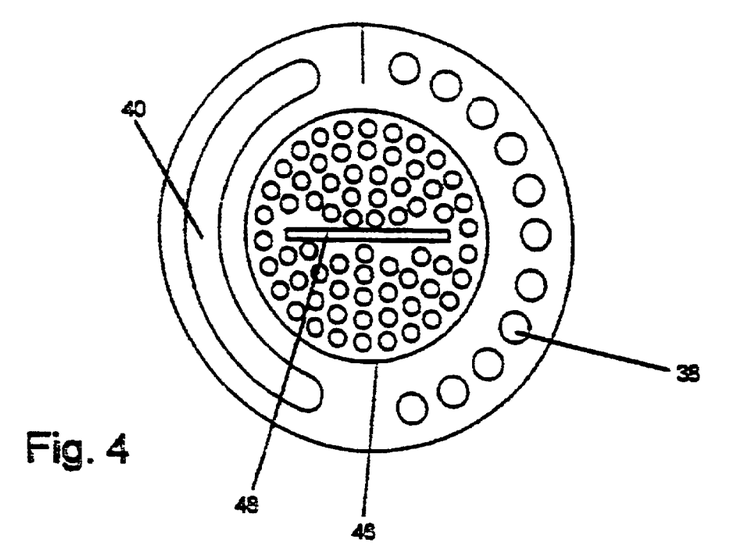
FIG. 4 is a view of the filter/valve arrangement according to FIG. 2, seen from below.
Figure 5:
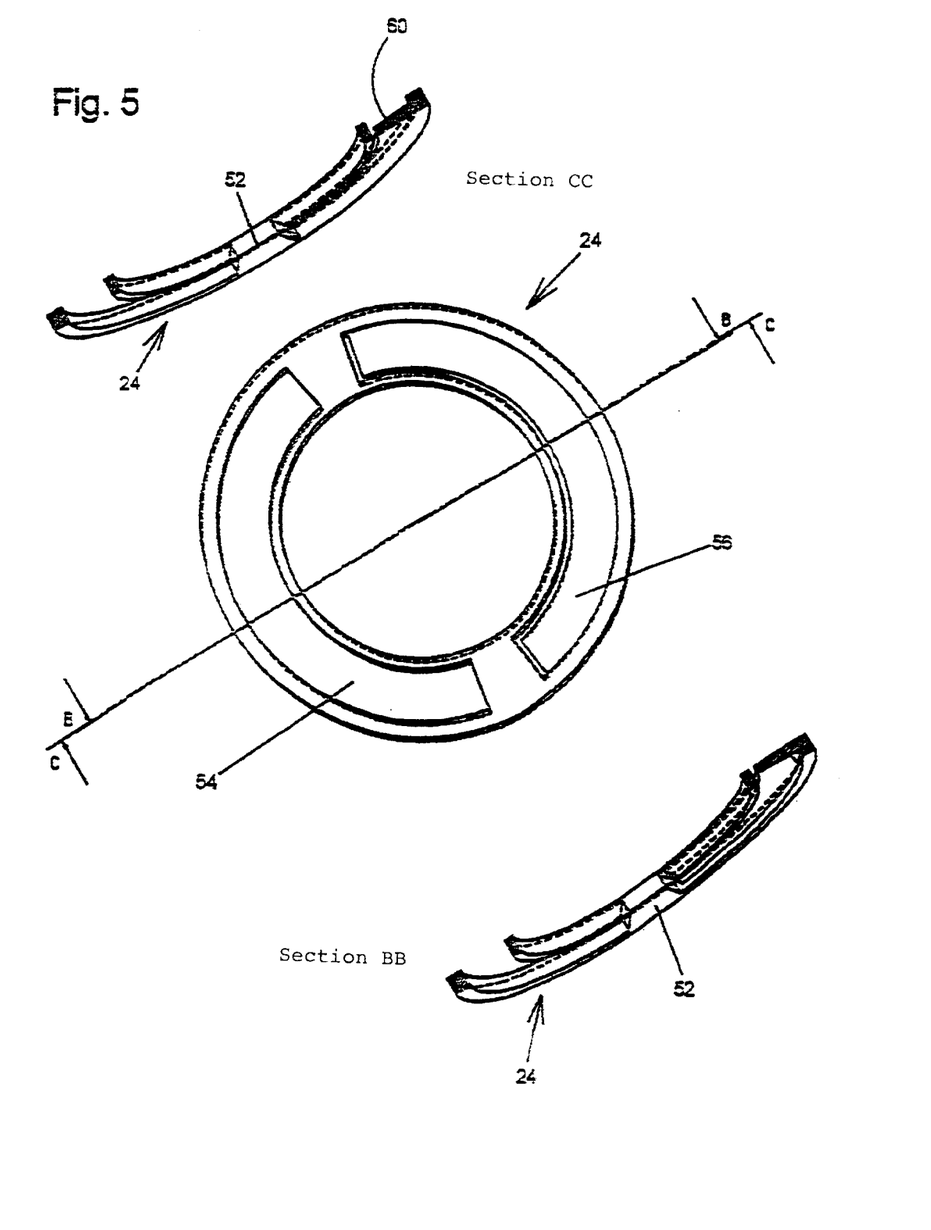
FIG. 5 shows a perspective view of the valve ring enclosing the filter.

Two valve rings 22, 24 are clamped into a circular opening of the intermediate cover 12, which valve rings 22, 24 between them clamp the edge 26 of the opening of the intermediate cover 12. The two valve rings 22, 24 are of identical design, but are offset by 180° in terms of their position and placed in opposite directions (FIG. 5). The valve rings could also be made in one piece. The valve rings 22, 24 bear a filter holder plate 28 which is provided in the central area with perforation holes 29 for the exchange of media and which on one side, over the valve ring 22, has an arc-shaped slit 30 and, on the other side, over a semicircle, has holes 32. From the bottom, the valve ring 22 is supported by an annular frame 34 which is L-shaped in cross section and whose vertical branch is braced with the filter holder plate 28 by screws 36. The horizontal branch of the annular frame has, on one side under the arc-shaped slit 30, holes 38, and, on the other side under the holes 32, an arc-shaped slit 40. The valve ring 22 is made of an elastic material and it is clamped sealingly against the edge of the intermediate cover by the screws 36. At the top and bottom, the valve ring 22 is enclosed from the outside by annular walls 42 which are made integral with the filter holder plate 28 or the annular frame 34, for example as a cup-shaped drawn part, injection-molded part or rotary part. The vertical branch of the annular frame 34 has an internal thread 44 into which a perforated bracing disk 46 with hand grip 48 can be screwed. A filter disk 50 is clamped sealingly between the filter holder plate 28 and the bracing disk 46.

The valve ring 22 has an annular chamber which is divided by dividing walls 52 into two circular arc-shaped chambers 54 and 56 which extend almost 180° between the dividing walls 52. In the left-hand circular arc section according to FIG. 2, the valve ring has a lip seal 58 which extends from the outside inward over the chamber 54, which is prestressed with a predetermined force against the filter holder plate 28 and seals off the holes 32. In the area of the other arc-shaped chamber 56, the valve ring 22 has a lip seal 60 which extends from the outside inward and which is prestressed against the horizontal branch of the annular frame 34 and seals off the holes 38.

In this way, the filter disk 50 is fixed immovably relative to the intermediate cover 12 via the holding frame, which is formed by the annular frame 34, the valve ring 22 and the filter holder plate, and braced via the bracing disk 46. If, during the sterilizing process, the pressure difference between outside and inside exceeds a value which can no longer be compensated via the filter 50, the lip seal 58 is then lifted from the filter holder plate 28 so that an exchange of media can take place via the holes 32, the chamber part 54 and the arc-shaped slit 40. If, by contrast, during the sterilizing process, the pressure difference between the inside of the sterilizing container and the sterilizer exceeds a predetermined value, the lip seal 60 is then lifted from the holes 38 and a bypass is established via the chamber section 56 and the arc-shaped slit 30. While the valve arrangement opens and closes again automatically under the elastic prestressing of the lip seals, the filter holder plate remains immovably clamped in position, so that no disturbances can occur if parts of the container contents come into the proximity of the filter. In order to avoid disturbances also in the area of the lip seals 58 and 60, and to ensure perfect valve functioning even when matter on the inside or outside comes near to the through-openings or slits, these can be bridged for protection. This can be done, for example, by forming bridges across the holes or slits as these are being punched out.

According to the illustrative embodiment in FIGS. 6 to 9, the intermediate cover 12A is designed as an upper filter holder plate and for this purpose has a perforation 29A below which the filter disk 50A is braced. It will be evident from FIGS. 6 and 9 that these can be filters of any type, namely, as sketched on the right-hand side, a thin flat filter, and, as shown on the left-hand half, a thicker, filter, for example a ceramic filter or volume filter.

This filter 50A is braced from below against the intermediate cover 12A by a filter holder element, and a sealing ring 64 provides a seal between filter 50A and intermediate cover 12A on the outer edge. This filter holder plate is fixed on the outer edge of the intermediate cover 12A in any desired way, for example by clamping or screwing. An important point here is that no cavities remain upon deliberate dismantling (e.g. filter replacement or filter inspection). This ensures excellent cleaning possibilities without wash shadows. The filter holder plate 62 is provided with perforation holes 66. Arranged all around the filter disk 50A, between the intermediate cover 12A and the filter holder plate 62, there is an annular chamber 68 in which a valve ring 70 is braced between intermediate cover 12A and filter holder;plate 62. Two diametrically opposite dividing walls 72 of the valve ring 70 divide the annular chamber 68 into two circular arc sections. In the arc chamber on the left-hand side according to FIGS. 6 to 8, the valve ring 70 bears sealing lips 74 which are prestressed against the intermediate cover 12A and close off the opening 76 of the intermediate cover arranged in this area. On the right-hand side according to FIGS. 6 to 8, the valve ring 70 has sealing lips 78 which are prestressed down toward the filter holder plate 62 and which cover the openings 80 in this arc section. Under the openings 76, the filter holder plate 62 has openings 82 via which an exchange of media can take place if an external overpressure develops, after the sealing lips 74 are lifted from the openings 76. Over the openings 80, the intermediate cover 12A has openings 84 via which the exchange of media can take place if the sealing lip 78 is lifted from the openings 80 by internal overpressure.

Figure 6:
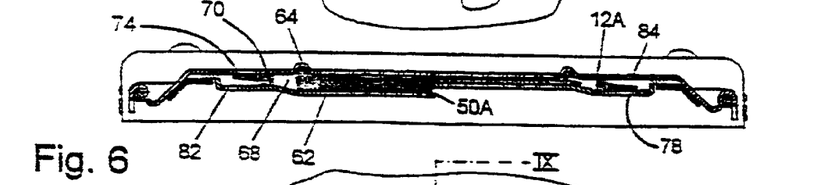
FIGS. 6 to 9 show a filter/valve combination similar to that in FIGS. 1 to 5, but in which the upper filter holder plate is formed by the intermediate cover itself.
Figure 7:
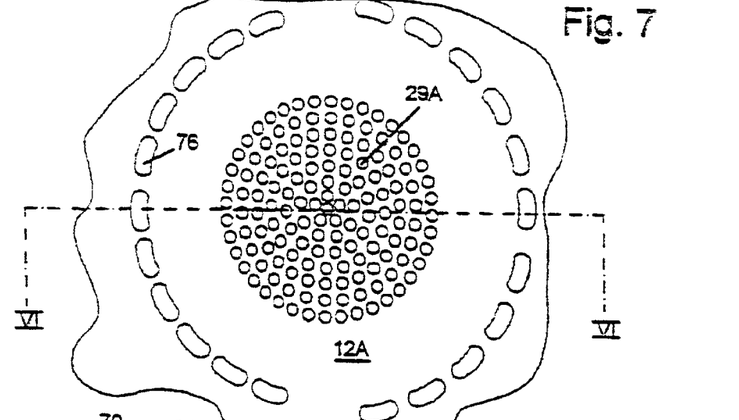
Figure 8:
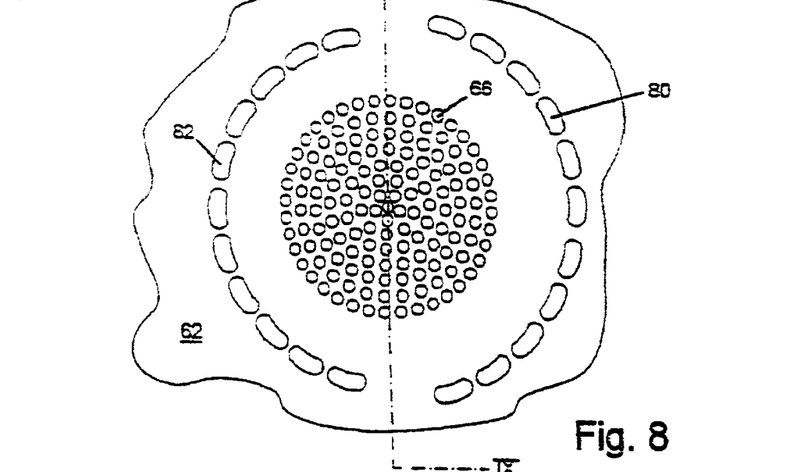
Figure 9:
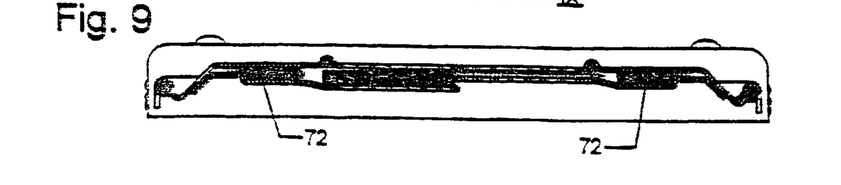
Figure 10:
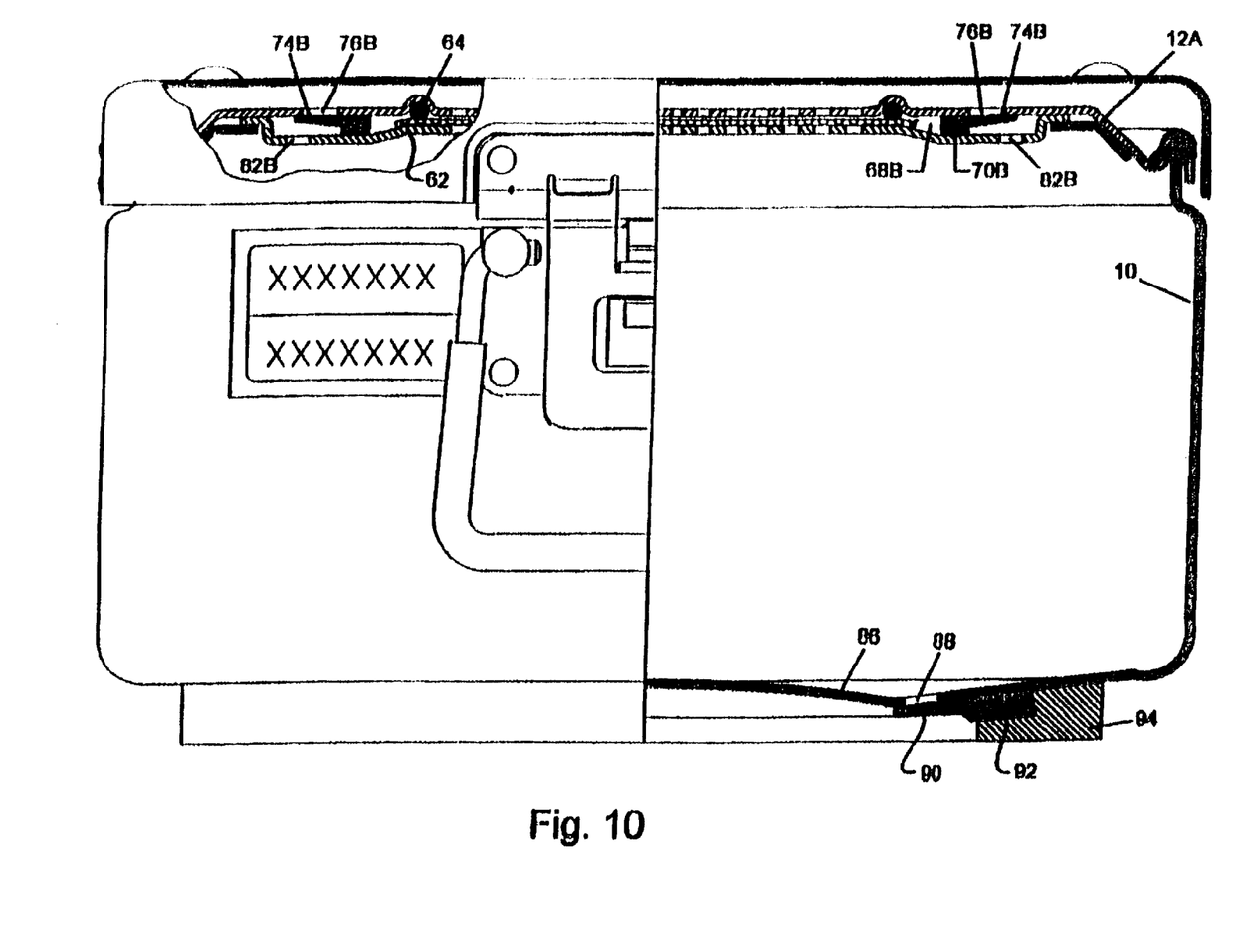
FIG. 10 is a partial sectional view of a sterilizing container which is provided in the intermediate cover with a filter/inlet valve combination and bears the outlet valve in the bottom part.

FIG. 10 shows the cross-sectional view of a sterilizing container in which a filter/inlet valve combination is arranged in the intermediate cover 12A. This combination essentially corresponds to the structure according to FIGS. 6 to 9, with the difference that a continuous, undivided annular chamber 68B is provided and the valve ring 70B is of continuous design, as is illustrated in FIG. 6 for the left annular chamber. That is to say, its sealing lips 74B bear on the intermediate cover 12A over the entire circular arc area and close the openings 76B of the intermediate cover 12A. If an external overpressure develops, the sealing lip 74B lifts from the intermediate cover and the route between the openings 76B and the openings 82B.

In this illustrative embodiment according to FIG. 10, the bottom 86 of the lower part 10 of the container is provided with an upwardly convex curvature and the bottom edge is beveled off downward so as to give a recessed annular channel which is provided with outlet openings 88. Bearing against these outlet openings 88 from below is the sealing lip 90 of a valve ring 92, which sealing lip 90 lifts in the event of a predetermined pressure difference developing, and thus allows air/vapor to flow out and at the same time permits escape of condensation water which has accumulated in the annular channel. The valve ring 92 is clamped in a stand frame 94. This arrangement affords advantages, particularly with the filter provided for the invention, because the water above the valve is then forced out first. The ensuing strong downward/outward flow then entrains isolated, remaining droplets with it and thus permits complete drying upon steam sterilization.

Figure 11:
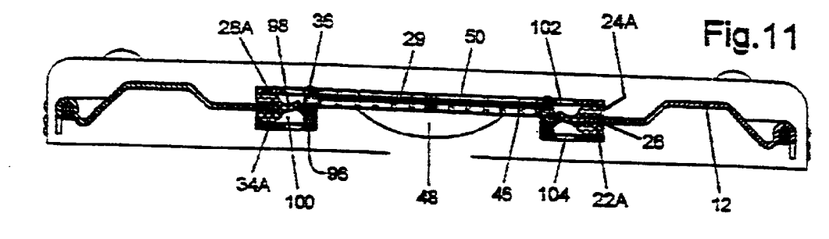
FIG. 11 shows a cross section of a modified embodiment of a filter/valve combination arranged in the intermediate cover.
Figure 12:
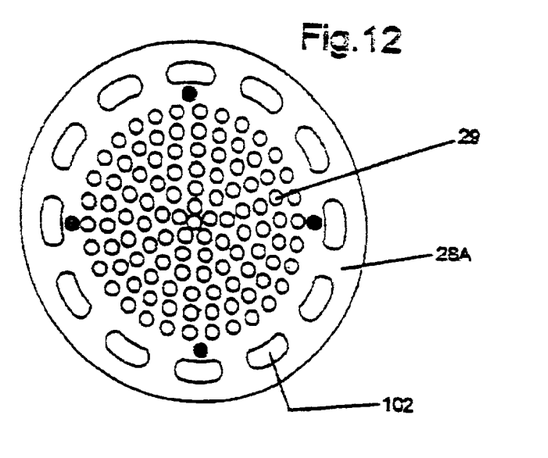
FIG. 12 is a plan view of the filter/valve combination from above.
Figure 13:
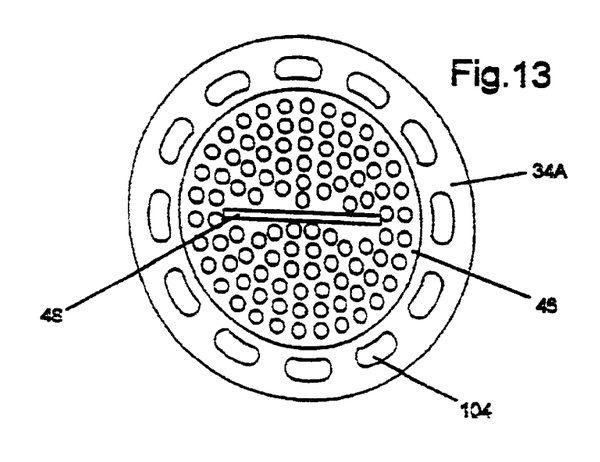
FIG. 13 is a plan view of the filter/valve combination according to FIG. 11, seen from below.

In the illustrative embodiment according to FIGS. 11 to 13, a valve ring 22A is pushed with its outer annular groove 24 onto the edge 26 of the opening of the intermediate cover 12. This valve ring 22A is clamped between an upper filter holder plate 28A and a lower annular frame 34A, which corresponds to the annular frame 34 according to FIG. 2. The filter holder plate 28A is joined via screws 36 to the vertical branch of the annular frame 34. The vertical branch of the annular frame 34A has, in the central section, a rib 96 of triangular cross section. This rib 96 acts as a valve seat for a sealing lip 98 which protrudes inward from the valve ring 22A over the entire periphery. The sealing lip 98 is designed as a continuous annular lip and is situated in an annular chamber 100 between the valve ring 22A and the vertical branch of the annular frame 34A. The filter holder plate has openings 102 above the annular chamber 100, and the horizontal branch of the frame 34A has openings 104. As in the illustrative embodiment according to FIG. 2, a perforated bracing disk 46 is screwed into the frame 34A and braces the filter disk 50 against the filter holder plate. In the position shown in FIG. 11, the sealing ring lip 98 bears sealingly on the valve seat, i.e. the rib 96, from above. When a predetermined pressure difference occurs, with an internal pressure which has increased relative to the external pressure, the sealing lip 98 is lifted and frees the bypass flow path from the openings 104 to the openings 102. If a predetermined pressure difference builds up in the opposite direction, the lip 98 slips past the rib and opens the flow path from the openings 102 to the openings 104. If this overpressure is then reduced, the sealing lip 98 bears from below on the rib 96, on account of its elasticity, and provides a closure which is tight to microorganisms.

In this illustrative embodiment too, there are no moving parts except for the sealing lip inside the annular chamber 100, which is enclosed all around, since the filter/valve combination is braced immovably on the intermediate cover 12. Of course, this filter/valve combination could also be arranged in a side wall of the container or in a cover placed sealingly on the lower part of the container.

Figure 14:
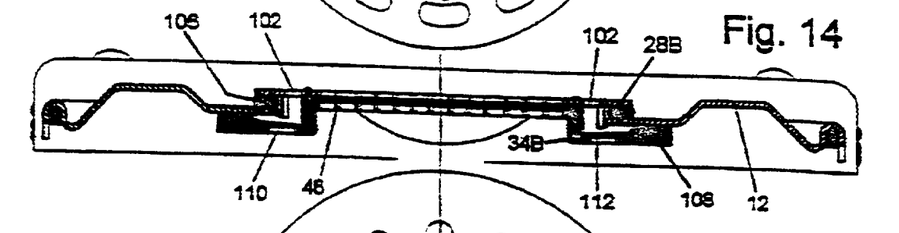
FIG. 14 is a cross section of a further modified embodiment of a filter/valve combination.
Figure 15:
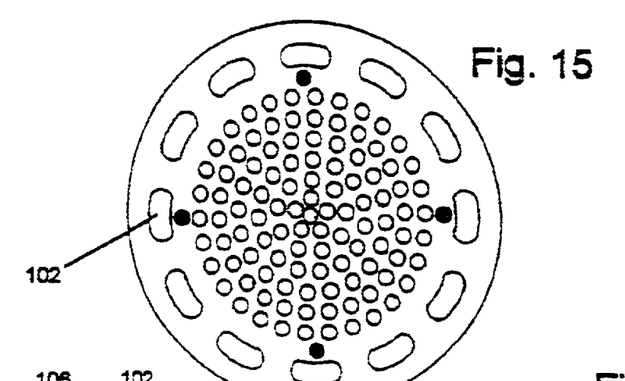
FIG. 15 is a plan view according to FIG. 14, seen from above.
Figure 16:
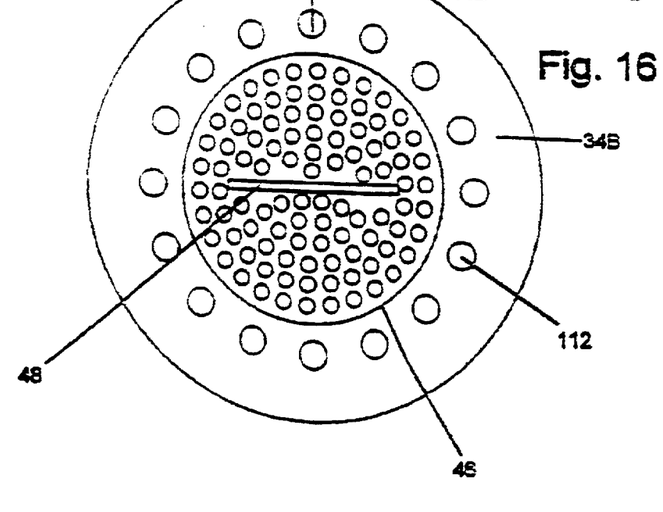
FIG. 16 is a plan view according to FIG. 14, seen from below.

A further illustrative embodiment is shown in FIGS. 14 to 16. Here, the upper filter holder plate 28B is supported at the periphery on a sealing ring 106 which is made of soft rubber or foamed porous material and which bears on the opening edge of the intermediate cover 12. As in the illustrative embodiment according to FIGS. 2 and 11, the filter holder plate is screwed to an annular frame 34B, into which a perforated bracing disk 46 is screwed in turn. The horizontal branch of the annular frame 34B bears a sealing ring 108 braced from below against the edge of the intermediate cover 12, with an inwardly directed sealing lip 110 which covers the openings 112 of the bracing disk 46 in the rest state.

If, during the sterilizing process, the external pressure builds up relative to the internal pressure, the sealing ring 28B is squeezed together when a predetermined pressure difference is reached, and the annular frame.34 is pressed down with the filter holder plate, as a result of which the sealing ring 108 is lifted from the opening edge of the intermediate cover 12, so that a bypass is created via the openings 102 in the filter holder plate and the annular opening above the sealing ring 108. When a pressure difference occurs in the opposite direction, the sealing lip 110 is lifted from the openings 112, and a bypass is created in the opposite direction via the openings 102. Although the whole filter structure with holding frame moves here in the event of an external overpressure, suitable coverings can be used to prevent the container contents from disturbing or blocking the function of the valve arrangement.

FIGS. 17 to 20 show a further illustrative embodiment. Here, a sealing ring 114 of soft rubber with an outer annular groove is pushed onto the edge of a cover opening of the intermediate cover 12. The edge of the filter holder plate 28 lies on the sealing ring 114. Bearing from below against the sealing ring 114 is the horizontal branch of the annular frame 34, into which the bracing disk 46 is screwed, pressing the filter disk 50 against the filter holder plate. Arranged between the sealing ring 114 and the annular frame 34 there are two circular arc-shaped chambers 54 and 56 which are sealed off from one another by inwardly extending dividing walls 116 of the sealing ring 114. The chamber 56 communicates with the outside via openings 118 in the filter holder disk 28, and the chamber 54 communicates with the inside of the container via openings 120 in the bracing disk 46.

Figure 17:
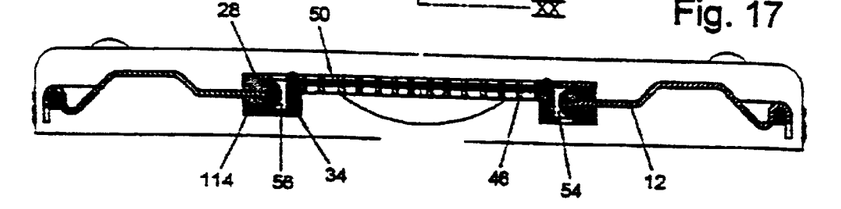
FIG. 17 is a sectional view of a further embodiment of a filter/valve combination, sectioned along the line XVII—XVII according to FIG. 18.
Figure 18:
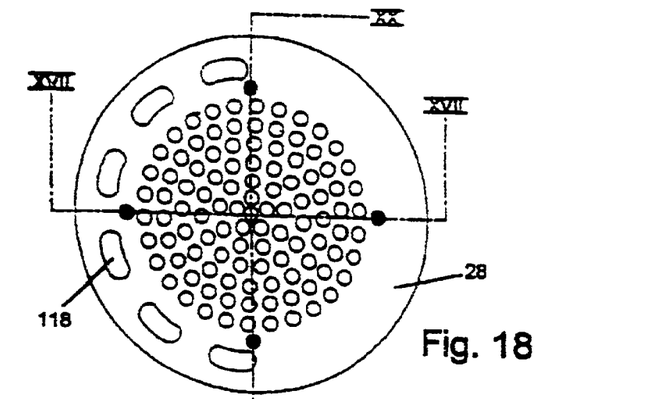
FIG. 18 is a view of the filter/valve combination according to FIG. 17, seen from above.
Figure 19:
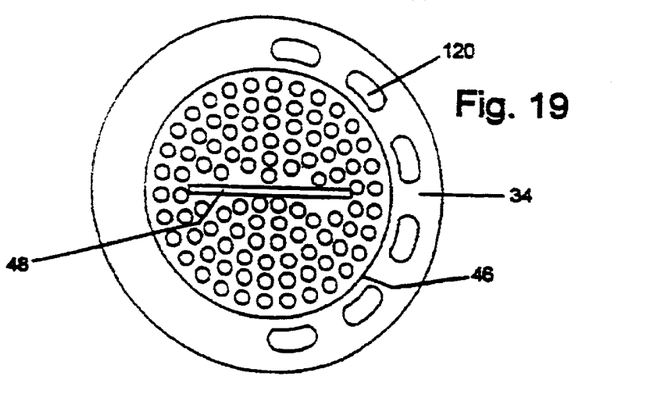
FIG. 19 is a view of the filter/valve combination according to FIG. 17, seen from below.
Figure 20:
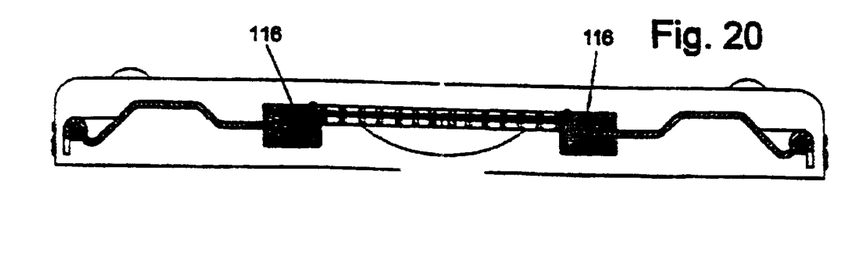
FIG. 20 is a section along the line XX—XX according to FIG. 18.

In the event of an external overpressure, the upper part of the sealing ring 114 is squeezed together, and the horizontal branch of the annular frame 34 is lifted from this sealing ring, as a result of which a bypass is created via the openings 118. Conversely, in the event of an overpressure from the inside, the underside of the sealing ring 114 is squeezed together, as a result of which the filter holder plate is lifted with its edge from the sealing ring and frees a bypass via the openings 120.

The sterilizing container according to the invention is suitable not only for steam sterilization, but also for sterilization by gas or plasma. By means of the sterilizing container according to the invention, a sterilized condition is preserved until intentional opening of the container, since by using the invention—and without hindering sterilization—substantially better, denser filters can be used.

The invention can be used not only for clinical sterile material, but also for any other items to be sterilized, for example in the pharmaceutical industry.

To protect the through-openings and to prevent matter from penetrating into the openings and impairing the function of the valves, a protective covering can be provided, which protective covering can be obtained by bridging the holes as they are being punched out.

The preferred embodiment is the circular design, but rectangular filter/valve combinations are also possible.

What is claimed is:

1. Sterilizing container for holding surgical instruments or other sterilizing material during sterilization and for maintaining the sterilized condition during storage and transportation, comprising:
   a body portion defining an inside and having at least one opening to permit exchange of media during sterilization;
   a filter fitted sealingly into the opening and adapted so as to permit at least a limited exchange of media after sterilization and form a barrier to microorganisms during storage;
   a self-closing inlet valve that opens toward the inside of the container when a predetermined pressure difference between external pressure and internal pressure is exceeded;
   a self-closing outlet valve that opens outward when a predetermined pressure difference between internal pressure and external pressure is exceeded;
   the filter is clamped in a holding frame and is supported all round on the holding frame with a form fit;
   the holding frame is clamped on an edge of the container opening; and
   at least the inlet valve is arranged inside the holding frame, the inlet and outlet valves being adapted to be permanently closed after sterilization.

2. Sterilizing container according to claim 1, wherein the filter and both valves are arranged in a single, common opening of the container, and both valves are integrated in the holding frame.

3. Sterilizing container according to claim 1, wherein the filter/valve combination (20) is braced with its holding frame on the edge (26) of the opening and is supported all round with a form fit.

4. Sterilizing contain according to claim 1, wherein the filter (50) has two sides and is supported on both sides by a perforated plate.

5. Sterilizing container according to claim 4, wherein the filter/valve combination (20) is of circular design, a filter holder plate (28) supporting a filter disk (5) at the top is braced (36) with an annular frame (34), and a bracing disk supporting the filter (5) from the other side is fitted sealingly into an internal thread (44) of the annular frame (34).

6. Sterilizing container according to claim 5, wherein the valves are designed as lip valves (58, 60) of circular arc shape and are formed inside the annular frame (34).

7. Sterilizing container according to claim 6, wherein the valves are formed by a two-part, circumferential sealing ring (22, 24) which is clamped onto the opening edge (26).

8. Sterilizing container according to claim 7, wherein the valve rings (22, 24) together form two circular arc-shaped chambers (54, 56) which are separated from each other by dividing walls (52), and one circular arc-shaped chamber (54) is equipped at the top with a lip seal (58) which acts against openings (32) of the filter holder plate (28), whereas, in the other circular arc-shaped chamber (56), a lip seal (60) is prestressed against frame openings (38) which lead to the inside of the container.

9. Sterilizing container according to claim 1, wherein the holding frame is formed by one of an intermediate cover (12A) and another container part and braced thereon, with interpositioning of a filter (50A), by a filter holder plate (72), and lip seals (74, 78) are arranged in an annular chamber (68) formed between intermediate cover (12A) and filter holder plate (62), which annular chamber (68) is divided circumferentially by dividing walls (72) so that, in one annular chamber part, the lip seals (74) bear against openings (76) of the intermediate cover (12A) and, in the other annular chamber part, the lip seals bear against openings (80) of the filter holder plate.

10. Sterilizing container according to claim 1, wherein the inlet valve is an encircling inlet valve (74) arranged in a chamber enclosing the filter (50) in one of the cover and the container, and the outlet valve (90) is arranged as a condensate valve in an annular bottom recess in the bottom of the container.

11. Sterilizing container according to claim 10, wherein the outlet valve is formed by a valve ring (92) which is braced on the bottom of the container and which has an inwardly extending valve lip (90) elastically prestressed against bottom openings (88), whereby this arrangement simultaneously functions as a condensate bleeder valve.

12. Sterilizing container according to claim 1 wherein a valve ring (22A) braced on the container edge (26) is fitted in an annular frame (34A), which valve ring (22A) bears an inwardly directed sealing lip (98) which interacts with an annular rib (96) of the annular frame (34A).

13. Sterilizing container according to claim 12, wherein the sealing lip is configured and adapted so that when a predetermined pressure difference is exceeded, the sealing lip (98) can be lifted over the rib (96) to open a bypass route.

14. Sterilizing container according to claim 5, wherein the annular frame (34B) is configured and adapted so that the frame can be lifted out relative to the container edge to open, a bypass route.

15. Sterilizing container according to claim 14, wherein the frame has a sealing ring (114) which is made of rubber and which, when a predetermined pressure difference develops, can be squeezed together to free a bypass route.

16. Sterilizing container according to claim 15, wherein the rubber seal (114) has an outer annular groove with which it is fitted into the opening edge of the container, and the annular chamber formed between sealing ring (114) and annular frame (34) is divided by walls (116) into two circular arc-shaped chambers which, on the one hand, lead outward via openings (118) in the filter holder plate (28) and, respectively, on the other hand, lead toward the inside of the container via openings (120) in a bracing disk.

17. Sterilizing container according to claim 14, wherein the valve has a ring designed as a rubber ring arranged between the opening edge and an edge of the filter holder plate, and a circumferential annular seal (108), provided with an all-round sealing lip (110), is arranged between container edge and frame and closes off openings (I 12) leading toward the inside of the container.

18. Sterilizing container according to claim 17, wherein the annular frame (34b) is adapted so that it can be lifted inward with the sealing ring (108), the sealing ring (28B) being squeezed together.

19. Sterilizing container according to claim 1, wherein the filter is a volume filter.

20. Sterilizing container according to claim 1, wherein the volume filter is accommodated in an encapsulated housing which is sealingly fitted into the frame (34).

* * * * *